(12) United States Patent
Dong et al.

(10) Patent No.: US 11,779,310 B2
(45) Date of Patent: Oct. 10, 2023

(54) SYSTEMS AND METHODS FOR MAGNETIC RESONANCE ELASTOGRAPHY WITH UNCONSTRAINED OPTIMIZATION INVERSION

(71) Applicant: Ohio State Innovation Foundation, Columbus, OH (US)

(72) Inventors: Huiming Dong, Columbus, OH (US); Rizwan Ahmad, Hilliard, OH (US); Arunark Kolipaka, Delaware, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 977 days.

(21) Appl. No.: 16/406,488

(22) Filed: May 8, 2019

(65) Prior Publication Data

US 2019/0343488 A1 Nov. 14, 2019

Related U.S. Application Data

(60) Provisional application No. 62/668,426, filed on May 8, 2018.

(51) Int. Cl.
*A61B 8/08* (2006.01)
*G01S 15/89* (2006.01)
*G01R 33/563* (2006.01)
*A61B 5/05* (2021.01)
(Continued)

(52) U.S. Cl.
CPC ............... *A61B 8/485* (2013.01); *A61B 5/05* (2013.01); *G01R 33/56358* (2013.01); *G01S 15/8906* (2013.01); *A61B 5/055* (2013.01); *A61B 5/7257* (2013.01); *G01N 2291/02827* (2013.01)

(58) Field of Classification Search
None
See application file for complete search history.

(56) References Cited

U.S. PATENT DOCUMENTS

2011/0060210 A1* 3/2011 Ehman ................ A61B 5/4244
600/587
2013/0131490 A1* 5/2013 Huston, III ...... G01R 33/56358
600/410

(Continued)

OTHER PUBLICATIONS

Ramani et al., "Parallel MR Image Reconstruction using Augmented Lagrangian Methods", IEEE Transactions on Medical Imaging, vol. 30, No. 3, Mar. 2011, pp. 694-706. (Year: 2011).*

(Continued)

*Primary Examiner* — Katherine L Fernandez
(74) *Attorney, Agent, or Firm* — Meunier Carlin & Curfman LLC (57) ABSTRACT

Systems and methods for magnetic resonance elastography (MRE) are disclosed. In one embodiment, MRE data corresponding to mechanical waves in tissue of interest of a subject is acquired. The MRE data is associated with stiffness of the tissue. The method also includes generating, based on the MRE data, a stiffness map representing stiffness of the tissue. Generating the stiffness map includes performing an unconstrained optimization cost function that is configured to reduce noise in the acquired MRE data and achieve inversion of the reduced-noise data.

21 Claims, 8 Drawing Sheets
(7 of 8 Drawing Sheet(s) Filed in Color)

(51) Int. Cl.
A61B 5/00 (2006.01)
A61B 5/055 (2006.01)

(56) References Cited

U.S. PATENT DOCUMENTS

2015/0309140 A1* 10/2015 Trzasko ........... G01R 33/56358
 324/309
2016/0232690 A1* 8/2016 Ahmad ................ G01R 33/445
2018/0292499 A1 10/2018 Meyer et al.

OTHER PUBLICATIONS

Kruse SA, Smith JA, Lawrence AJ, Dresner MA, Manduca A, Greenleaf, JF and Ehman RL. Tissue characterization using magnetic resonance elastography: preliminary results. Physics in medicine and biology 2000;45(6):1579-1590.

Manduca A, Oliphant TE, Dresner M, Mahowald J, Kruse SA, Amromin E, Felmlee JP, Greenleaf JF, Ehman RL. Magnetic resonance elastography: Non-invasive mapping of tissue elasticity. Med Image Anal 2001;5(4):237-254.

Muthupillai R, Lomas D, Rossman P, Greenleaf JF. Magnetic resonance elastography by direct visualization of propagating acoustic strain waves. Science 1995;269(5232):1854-1856.

Oliphant TE, Manduca A, Ehman RL, and Greenleaf JF. Complex-valued stiffness reconstruction for magnetic resonance elastography by algebraic inversion of the differential equation. Magnetic resonance in Medicine 2001;45(2): 299-310.

Paige CC and Saunders MA, LSQR: an Algorithm for Sparse Linear Equations and Sparse Least Squares, ACM Trans. Math. Soft. 1982;8:43-71.

Papazoglou S, Hamhaber U, Braun J, and Sack I. Algebraic Helmholtz inversion in planar magnetic resonance elastography. Physics in medicine and biology 2008;53(12):3147-3158.

Ting ST, Ahmad R, Jin N, Craft J, Serafim da Silveira J, Xue H, Simonetti OP. Fast implementation for compressive recovery of highly accelerated cardiac cine MRI using the balanced sparse model. Magnetic Resonance in Medicine 2017;77(4):1505-1515.

* cited by examiner

SYSTEMS AND METHODS FOR MAGNETIC RESONANCE ELASTOGRAPHY WITH UNCONSTRAINED OPTIMIZATION INVERSION

CROSS-REFERENCE TO RELATED APPLICATION

This application claims priority to, and benefit under 35 U.S.C. § 119(e) of, U.S. Provisional Patent Application No. 62/668,426, filed May 8, 2018, which is hereby incorporated by reference herein in its entirety as if fully set forth below.

STATEMENT REGARDING GOVERNMENT SUPPORT

This invention was made with government support under grant R01HL124096 awarded by the National Institutes of Health. The government has certain rights in this invention.

BACKGROUND

Magnetic resonance elastography (MRE) is a phase-contrast based magnetic resonance technique through which the shear stiffness of soft tissues can be estimated [1-3]. To obtain a desired stiffness map from the acquired MRE data, an inversion algorithm based on the Helmholtz equation may used [4-5]. However, correctly estimating shear stiffness can be challenging under the presence of noise because of the noise amplification from the Laplacian operation within the Helmholtz equation. Local-frequency estimation (LFE) is a known inversion method, but it usually yields estimation errors around edges [2].

It is with respect to these and other considerations that the various aspects of the present disclosure as described below are presented.

SUMMARY

In some aspects, the present disclosure relates to magnetic resonance elastography (MRE). MRE is a phase-contrast magnetic resonance technique in which the shear stiffness of soft tissues can be estimated for diagnosis of various diseases that are associated with stiffness change. To perform MRE according to some embodiments of the present disclosure, a mechanical driver generates external periodic mechanical waves in the tissue of interest, and subsequently, these wave images can be captured using a magnetic resonance scanner and then processed to obtain a stiffness map by a process known as inversion.

MRE inversion can be used to obtain stiffness of interest from measured MRE wave data. Accurate stiffness estimation can be critical in diagnosing different diseases, for example in order to distinguish diseased tissues from normal tissues. Many conventional MRE approaches have drawbacks due to, among other challenges, the presence of noise and complicated MRE wave patterns.

In some embodiments of the present disclosure, tissue stiffness can be accurately estimated in the presence of noise. According to some embodiments of the present disclosure, an MRE method (sometimes referred to herein as, or corresponding to, "optimization", "unconstrained optimization" and/or "optimization inversion" and which utilizes an unconstrained optimization cost function) is based on an unconstrained optimization process where noise is iteratively reduced from the measured wave data while the sparsity of the stiffness map in a sparsifying transform domain (e.g., wavelet transform domain, total variation domain, Fourier transform domain) is being explored, yielding more accurate tissue stiffness estimation in the presence of noise.

Among other benefits and advantages, aspects and embodiments of the present disclosure provide significant advantages over conventional inversion techniques in a variety of pre-clinical and clinical applications where MRE data is severely corrupted by noise. Those applications include MRE of different tissues and organs of a subject (e.g., human, animal, etc.) such as liver, brain, cardiovascular system, lung, breast, etc.

In one aspect, the present disclosure relates to a method which, in one embodiment, comprises the steps of: acquiring magnetic resonance elastography (MRE) data corresponding to mechanical waves in tissue of interest of a subject, wherein the MRE data is associated with stiffness of the tissue; and generating, based on the MRE data, a stiffness map representing stiffness of the tissue. Generating the stiffness map comprises performing an unconstrained optimization cost function that is configured to reduce noise in the acquired MRE data and achieve inversion of the reduced-noise data.

In another aspect, the present disclosure relates to a method which, in one embodiment, comprises the steps of: acquiring, by magnetic resonance scanning using scanning device, magnetic elastography (MRE) data corresponding to mechanical waves in tissue of interest of a subject, wherein the MRE data is associated with stiffness of the tissue. The method also includes generating, based on the MRE data, a stiffness map representing stiffness of the tissue. Generating the stiffness map comprises performing an unconstrained optimization cost function that is configured to reduce noise in the acquired MRE data and achieve inversion of the reduced-noise data. The method also includes: identifying, based on the stiffness map, a mechanical property change in the tissue; and identifying, based on the mechanical property change, an abnormal condition of the tissue.

In another aspect, the present disclosure relates to a system which, in one embodiment, comprises: a magnetic resonance device configured to acquire magnetic resonance elastography (MRE) data corresponding to mechanical waves in tissue of interest of a subject, wherein the MRE data is associated with stiffness of the tissue; and at least one processor coupled to the magnetic resonance device and configured to execute computer-readable instructions which cause the system to generate, based on the MRE data, a stiffness map representing stiffness of the tissue. Generating the stiffness map comprises performing an unconstrained optimization cost function that is configured to reduce noise in the acquired MRE data and achieve inversion of the reduced-noise data.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with the color drawing(s) will be provided by the Office upon request and payment of the necessary fee. Reference will now be made to the accompanying drawings, which are not necessarily drawn to scale.

DETAILED DESCRIPTION

In some aspects, the present disclosure relates to systems and methods for magnetic resonance elastography (MRE).

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest" (ROI).

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. For example, [3] refers to the $3^{rd}$ reference in the list, namely Kruse S A, Smith J A, Lawrence A J, Dresner M A, Manduca A, Greenleaf, J F and Ehman R L. Tissue characterization using magnetic resonance elastography: preliminary results. Physics in medicine and biology 2000; 45(6): 1579-1590. All references cited and discussed in this specification are incorporated herein by reference in their entireties and to the same extent as if each reference was individually incorporated by reference.

A detailed description of certain aspects of the present disclosure in accordance with various example embodiments will now be provided with reference to the accompanying drawings. The drawings form a part hereof and show, by way of illustration, specific embodiments and examples. In referring to the drawings, like numerals represent like elements throughout the several figures.

Although other aspects, embodiments, example implementations, and corresponding results according to various aspects of the present disclosure are presented below, an example context and discussion of an implementation of certain embodiments of the disclosure will now be discussed with respect to lung MRE. The functionality of the lung is closely associated with its gross topographically heterogeneous stiffness. For instance, emphysema is a lung disease in which the lung loses its parenchymal tissues over time, leading to reduced lung stiffness and thus causing hyperinflation and airway collapse. Performing lung MRE using conventional approaches is technically challenging due to low tissue density (0.2-0.3 g/cm$^3$) and very short T2* (less than 3 ms), which leads to noisy MRE data. This can result in inaccurate estimation of lung stiffness and thus limits its potential of being a robust diagnostic tool. In accordance with some embodiments of the present disclosure, noise is reduced from measured MRE data while the sparsity of stiffness map in the sparsifying transform domain (e.g., wavelet domain) is being explored, which can enable less noisy and more accurate stiffness estimation, thereby significantly facilitating the correct diagnosis of lung diseases.

Figure 1:
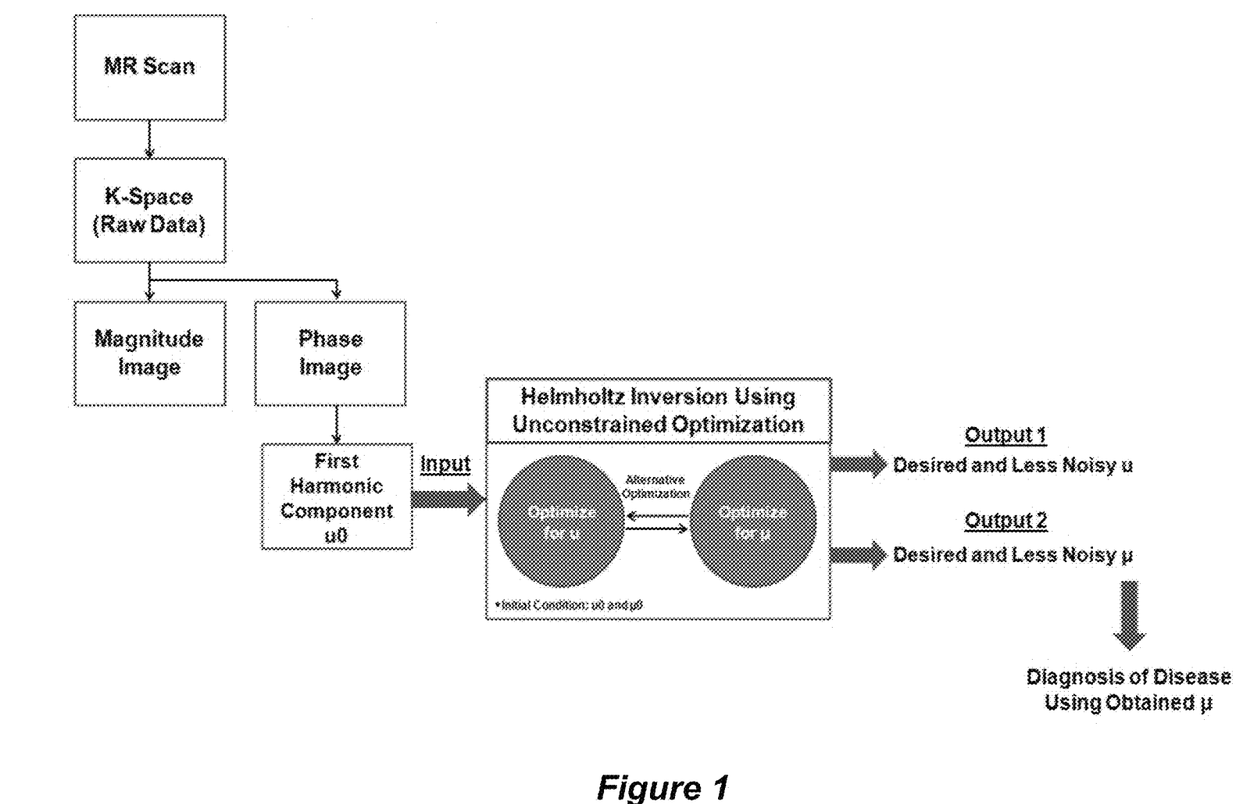
FIG. 1 is a flow diagram illustrating aspects of a method in accordance with some embodiments of the present disclosure.

FIG. 1 is a flow diagram showing various aspects of a method in accordance with an embodiment of the present disclosure. Note that the terms $\mu$, $\mu 0$, u, and u0 as mentioned here and illustrated in FIG. 1 are described in connection with an unconstrained optimization cost function according to some embodiments of the present disclosure as described in further detail below. As shown in the flow diagram of FIG. 1, a clinical MR scanner (see, e.g., FIG. 7 and corresponding discussion) is used to perform an MRE scan on the subject (e.g., human patient, animal, etc.) to acquire MRE data (see "MR Scan"). The acquired MRE data is stored in k-space (i.e., the raw data space of the MRE scan) before reconstruction (see "K-Space (Raw Data)"). A discrete Fourier transform is used to reconstruct the MR image from the obtained MRE data. After image reconstruction using the Fourier transform, a magnitude image and phase image will be recovered from the raw data (see "Magnitude Image", "Phase Image").

During MRE data acquisition, four MRE measurements are usually performed to acquire four phase offsets for yielding the measured first harmonic component ($u_0$). The first harmonic component $u_0$ (shown in FIG. 1 as "u0") is generated by applying a temporal discrete Fourier transform on the phase images from the acquired MRE measurements. The measured first harmonic component $u_0$ is the input of Helmholtz inversion using unconstrained optimization for calculating a tissue stiffness map ($\mu$) of the subject. Notably, the measured first harmonic component $u_0$ is usually noisy and thus can corrupt the correct estimation of tissue stiffness During Helmholtz inversion using unconstrained optimization (see block labeled "Helmholtz Inversion Using Unconstrained Optimization"), both the first harmonic component and tissue stiffness map are optimized alternatively using aspects of the present disclosure in which noise is reduced from the measured first harmonic component while the sparsity of the stiffness map in the sparsifying transform domain is being explored, resulting in more accurate estimation of tissue stiffness. Note that for the "Helmholtz Inversion Using Unconstrained Optimization", initial conditions are u0 and $\mu 0$.

As shown in FIG. 1, there are two outputs from the "Helmholtz Inversion Using Unconstrained Optimization" block: "Output 1" is a desired and less noisy first harmonic component u, and "Output 2" is a desired, more accurate and less noisy tissue stiffness map $\mu$. The desired, more accurate and less noisy tissue stiffness map $\mu$ is then used to assist diagnosis of disease of the subject (see "Diagnosis of Disease Using Obtained $\mu$"). The tissue stiffness map ($\mu$) of the subject can provide critical information about disease-associated mechanical property change of soft tissue, and thus can be used to diagnose different diseases, such as liver fibrosis and others mentioned above.

In accordance with some embodiments of the present disclosure, the cost function for Helmholtz inversion using unconstrained optimization is $$J(u, \mu) = \operatorname*{argmin}_{\mu,u} \left\| \frac{1}{c} \nabla^2 u * \mu - u \right\|_2^2 + \lambda_1 \|u - u0\|_2^2 + \lambda_2 \|\psi(\mu)\|_1 \quad \text{(Eq. 1)}$$

where $\nabla^2$ is the Laplacian operator, $c = -\rho \omega^2$, $\rho$ is density of the tissue of interest, $\omega$ is angular mechanical frequency associated with vibration of the tissue of interest, $\mu$ is the stiffness map of interest, u is pursued tissue displacement, u0 is measured tissue displacement from acquired MRE data, $\psi$ is a linear sparsifying transform, e.g., wavelet transform, total variation transform, or Fourier transform, and $\lambda_1, \lambda_2$ are regularization coefficients.

The angular mechanical frequency $\omega$ is mechanical frequency multiplied by $2\pi$. The mechanical frequency is the frequency of the vibration that is applied to vibrate the tissue of interest. This mechanical frequency can be determined based on the depth of the tissue in the body and dimensions of the tissue. Regularization coefficients $\lambda_1, \lambda_2$ can be empirically determined based on the particular implementation desired. For example, if one is calculating liver stiffness, then these parameters can be tuned to achieve a good stiffness map. Once determined, these coefficients can be used for liver stiffness calculation wherein the liver data is acquired using the same or similar imaging protocol. To determine if the stiffness is "good", the computed stiffness is compared to ground truth or the stiffness derived from gold standard method. In a different desired implementation, for example brain stiffness, these coefficients are retuned.

In accordance with some embodiments of the present disclosure, $\lambda_1, \lambda_2$ have the following effects: $\lambda_1$ controls the degree to which the pursued tissue displacement u deviates from the measured tissue displacement u0, wherein a small $\lambda_1$ allows more deviation and vice versa; and $\lambda_2$ controls the degree to which the pursued tissue stiffness map $\mu$ will be sparsified in the sparsifying transform $\psi$. A large $\lambda_2$ promotes sparsity of the pursued stiffness map in the sparsifying domain corresponding to the sparsifying transform and vice versa.

In accordance with some embodiments, the sparsifying transform $\psi$ is chosen based on the sparsity ($\|\psi(\mu)\|_1$) of the stiffness map in that sparsifying transform domain. For example, if the stiffness map has a sparser expression in wavelet transform domain than that in the Fourier transform domain, then the wavelet transform is used to explore the sparsity of the stiffness map.

In accordance with some embodiments of the present disclosure, when the measured tissue displacement is considerably noisy, the Laplacian operator $\nabla^2$ in Eq. 1 can be replaced with Laplacian of Gaussian operator LoG to further denoise the measured displacement data, resulting in more accurate stiffness calculation (see Eq. 2 below). In such embodiments, the cost function for Helmholtz inversion using unconstrained optimization is $$J(u, \mu) = \operatorname*{argmin}_{\mu,u} \left\| \frac{1}{c} LoG(u) * \mu - u \right\|_2^2 + \lambda_1 \|u - u0\|_2^2 + \lambda_2 \|\psi(\mu)\|_1 \quad \text{(Eq. 2)}$$

Using LoG is equivalent to applying Gaussian operator on the measured noisy data for smoothing and then applying the Laplacian operator on the smoothened data. Integrating the LoG operator can further denoise the data and yield more accurate stiffness map(s).

For both Eq. 1 and Eq. 2, the first term guarantees data fidelity when it is minimized since it describes the physical relationship between tissue displacement and its stiffness (i.e., the Helmholtz equation). The second regularization term allows the pursued displacement u to deviate from the noisy displacement u0 measured from MRE phase images. The third regularization term ensures the sparsity of stiffness map in a chosen sparsifying transform domain. Applied together, the regularization terms can effectively de-noise the measured displacement without blurring an object's edge and thus potentially generate more accurate stiffness maps. To solve this optimization problem, balanced fast iterative/shrinkage thresholding algorithm (bFISTA) and the least-square method (LSQR) can be used in optimizing the cost function.

Figure 7:
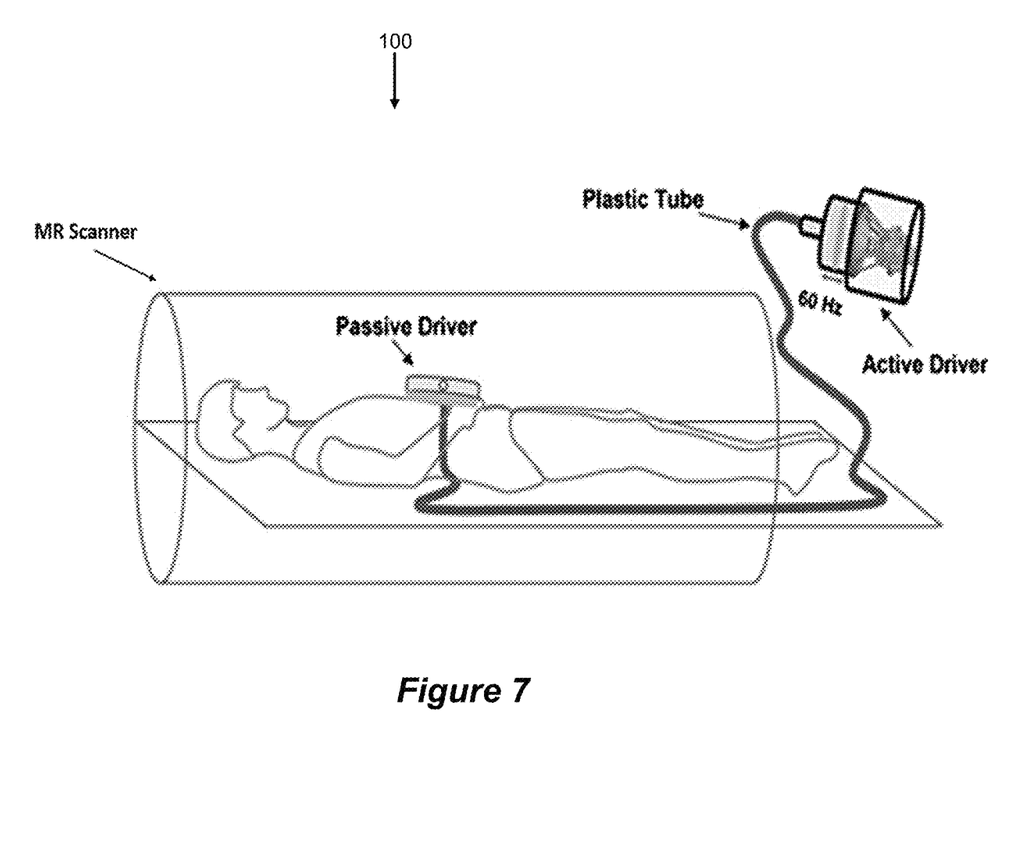
FIG. 7 is a diagram of a system capable of performing one or more aspects of MRE in accordance with various embodiments of the present disclosure.

FIG. 7 is a diagram of a system 100 capable of performing one or more aspects of MRE in accordance with various embodiments of the present disclosure. The system 100 is configured in this example for liver MRE measurements of a subject placed in a head-first supine position inside an MR scanner. Mechanical waves can be generated via an active pneumatic driver placed outside the scan room. A passive driver can be placed in an area of interest (e.g., abdomen, as shown) of the subject and the driver connected to the active driver through a plastic tube to induce the mechanical waves into the area of interest (e.g., liver). The frequency of the mechanical waves can be configured to a selected frequency (e.g., 60 Hz) for achieving optimal tissue penetration and spatial resolution.

It should be appreciated that any number and type of magnetic resonance scanning systems or components and/or mechanical drivers, including various types of commercially available medical imaging systems and components, may be used to practice certain aspects of the disclosed technology. Systems as described herein with respect to example embodiments are not intended to be specifically limited to the particular system shown in FIG. 7. Another non-limiting example illustration and discussion of a magnetic resonance scanner is disclosed in U.S. patent application Ser. No. 15/947,443 filed Apr. 6, 2018 (now U.S. Patent Application Publication No. 2018/0292499), for example shown in "FIG. 6" and described in the corresponding description, along with certain functionalities in combination with a computing system shown in "FIG. 7" of U.S. patent application Ser. No. 15/947,443, which is hereby incorporated by reference herein in its entirety.

One or more data acquisition or data collection steps as described herein in accordance with one or more embodiments may include acquiring, collecting, receiving, or otherwise obtaining data such as magnetic resonance imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

Figure 8:
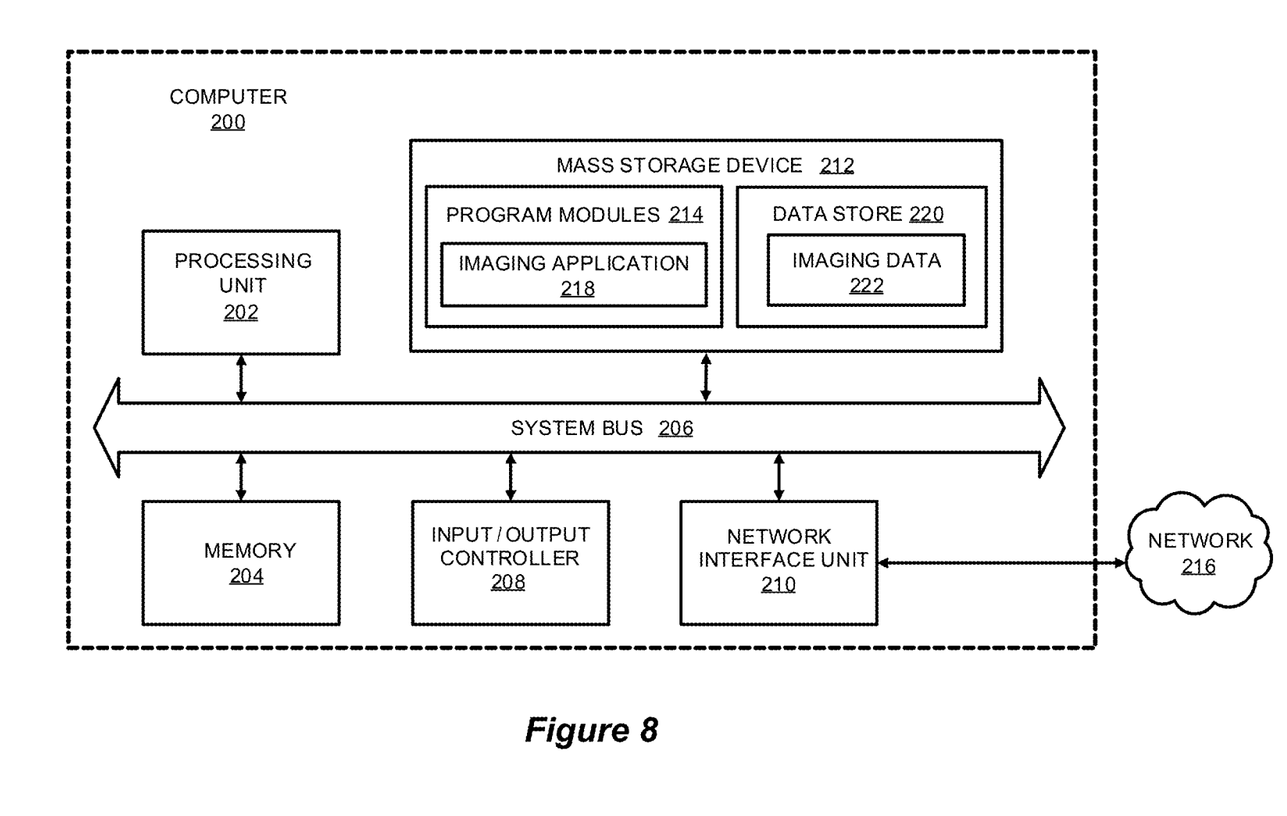
FIG. 8 is a computer architecture diagram showing a computing system capable of implementing one or more aspects of the present disclosure in accordance with various embodiments.

FIG. 8 is a computer architecture diagram showing a computing system capable of implementing one or more aspects of the present disclosure in accordance with various embodiments. A computer 200 may be configured to perform one or more functions associated with embodiments illustrated in one or more of FIGS. 1-7. The computer 200 may be operatively coupled to system 100 of FIG. 7. It should be appreciated that the computer 200 may be implemented within a single computing device or a computing system formed with multiple connected computing devices. As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 1-7 discussed herein. The program modules 214 may include an imaging application 218 for performing data acquisition and/or processing functions as described herein, for example to acquire and/or process data corresponding to magnetic resonance scanning by the MR scanner in FIG. 7, wave generation by the drivers shown in FIG. 7, and/or MRE data processing such as tissue map generation and/or analysis described herein in accordance with certain embodiments. The computer 200 can include a data store 220 for storing data that may include imaging-related data 222 such as acquired data from the implementation of magnetic resonance scanning in accordance with various embodiments of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more example embodiments and implementations illustrated in FIG. 1-7. The program modules 214 may also provide various tools or techniques by which the computer 200 may participate within the overall systems or operating environments using the components, flows, and data structures discussed throughout this description.

Example Implementations and Corresponding Results

Various aspects of the present disclosure may be still more fully understood from the following description of example implementations (EXAMPLE 1, EXAMPLE 2) and corresponding results and FIGS. 2-6. Some experimental data are presented herein for purposes of illustration and should not be construed as limiting the scope of the present disclosure in any way or excluding any alternative or additional embodiments.

Example 1

Simulated Data and Physical Phantom Measurements

In this example implementation, a four-band phantom with stiffness values of 10, 5, 2 and 1 kPa was simulated. Single-directional planar waves were assumed throughout the simulation. Additionally, MRE measurements were performed on a cylindrical phantom using a GRE MRE sequence on a 3T MR scanner (TimTrio, Siemens Healthcare, Erlangen, Germany). To compare the performance of an unconstrained optimization method according to embodiments of the present disclosure to LFE, the physical phantom data were acquired with number of averages of 1 and 30. Table 1a and 1b below summarize the simulation and MR imaging parameters.

TABLE 1a

Simulation Parameters

| Stiffness Value | 10, 5, 2 and 1 kPa |
|---|---|
| Mechanical Frequency | 60 Hz |
| No. of Phase Offsets | 4 |
| Field-of-View (FOV) | 280 × 280 mm$^2$ |
| Matrix Size | 256 × 256 |
| Added Noise Level | 1%, 3% and 5% Gaussian Noise |

Table 1a. Simulation Parameters

| Stiffness Value | 10, 5, 2, and 1 kPa |
|---|---|
| Mechanical Frequency | 60 Hz |
| No. of Phase Offsets | 4 |
| Field-of-View (FOV) | 280 × 280 mm$^2$ |
| Matrix Size | 256 × 256 |
| Added Noise Level | 1%, 3% and 5% Gaussian Noise |

Table 1b. Imaging Parameters

| Mechanical Frequency | 60 Hz |
|---|---|
| Motion Encoding Gradient Frequency | 60 Hz |
| Motion Encoding Direction | Slice Selection |
| No. of Phase Offsets | 4 |
| TE/TR | 21/50 ms |
| Slice Thickness | 5 mm |
| No. of Slices | 1 |
| Field-of-View (FOV) | 280 × 280 mm$^2$ |
| Reconstruction Matrix Size | 256 × 256 |
| Added Noise Level | 1%, 3% and 5% Gaussian Noise |

Data Processing and Analysis

Three levels of Gaussian noise (i.e., 1%, 3% and 5%) were added to the simulated and acquired wave images. The optimization inversion was performed using MATLAB (The MathWorks Inc., Natick. Mass.) and LFE was performed via MRElab (Mayo Clinic, Rochester, Minn.). Results were compared to the ground truth. Subsequently, root-mean-square error (RMSE) and maximum error was calculated. For the simulated data, ground truth was the input value without adding noise. For the cylindrical phantom, stiffness maps yielded by LFE and optimization methods using 30-average data were considered as the ground truth for its own inversion.

Results and Discussion

Figure 2:
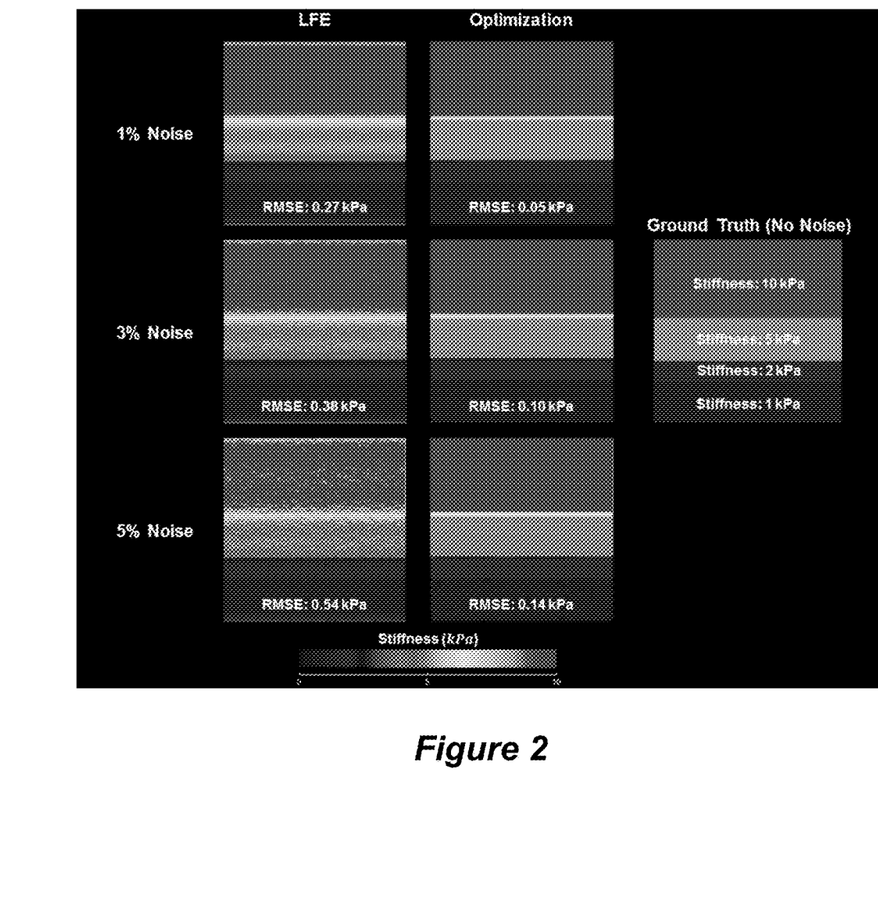
FIG. 2 illustrates stiffness maps of simulated data generated by LFE and by an optimization technique according to embodiments of the present disclosure.

The optimization method according to embodiments of the present disclosure yielded lower RMSE and more accurate stiffness maps in the simulated phantom when compared to LFE. FIG. 2 shows the stiffness maps obtained from both methods. Relatively noiseless stiffness maps were consistently observed in optimization-derived results. The RMSEs of LFE were 0.27, 0.38 and 0.54 kPa for 1%, 3% and 5% noise, respectively. The RMSEs of optimization were 0.05, 0.10 and 0.14 kPa for 1%, 3% and 5% noise, respectively.

Figure 3:
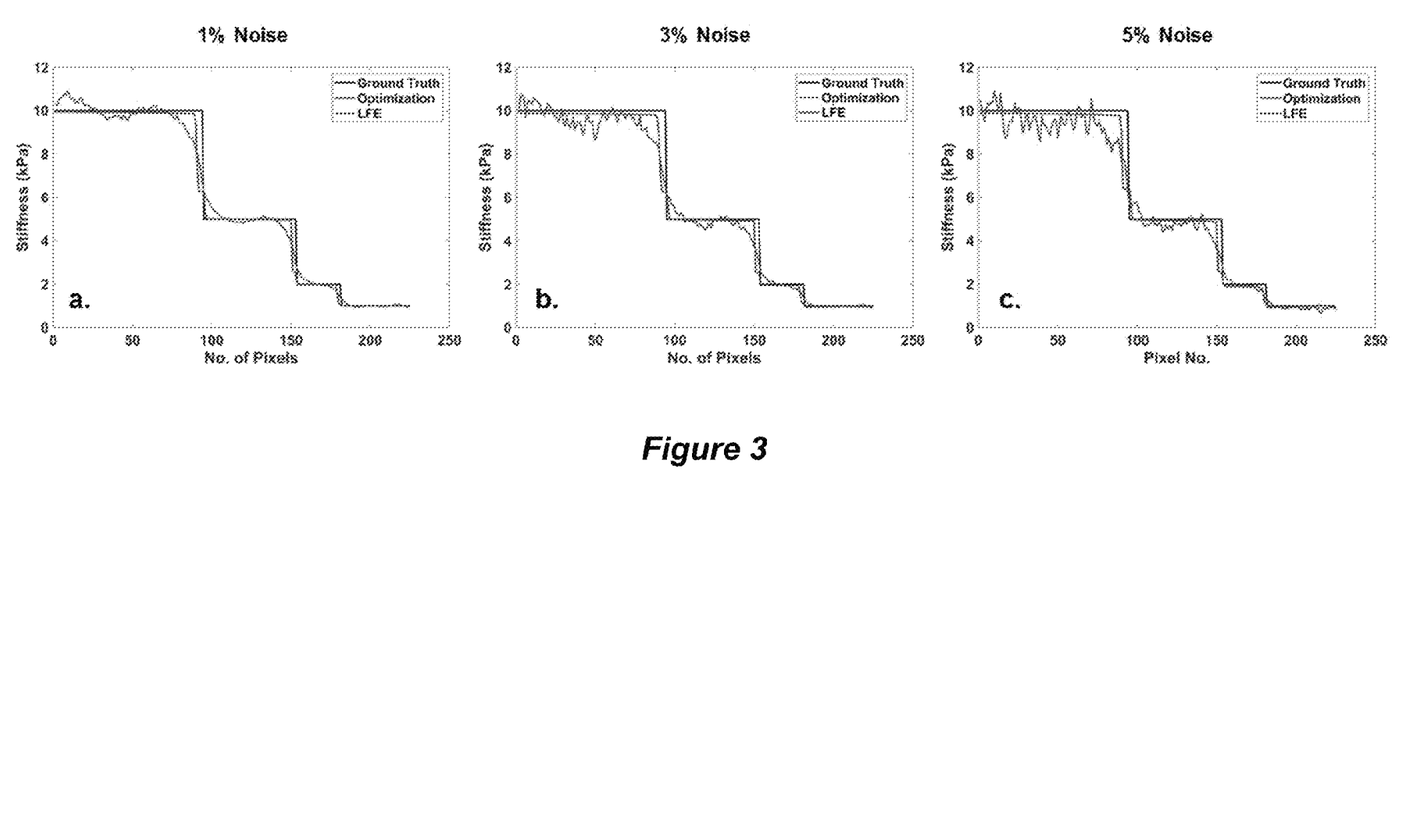
FIG. 3 illustrates the line profiles drawn from top to bottom at the center of the simulated data of the ground truth, optimization-derived (according to embodiments of the present disclosure), and LFE-derived stiffness maps for noise level of 1% (see "a."), 3% (see "b."), and 5% (see "c.").

Sharp stiffness transitions were preserved using optimization inversion. FIG. 3 displays the line profiles drawn from top to bottom at the center of the simulated data of the ground truth, optimization-derived and LFE-derived stiffness maps. LFE failed to maintain the sharp transition between different bands due to the well-known edge effect [2]. It was challenging for LFE to distinguish the 2 kPa band due to its small width and edge blurring effect.

Figure 4:
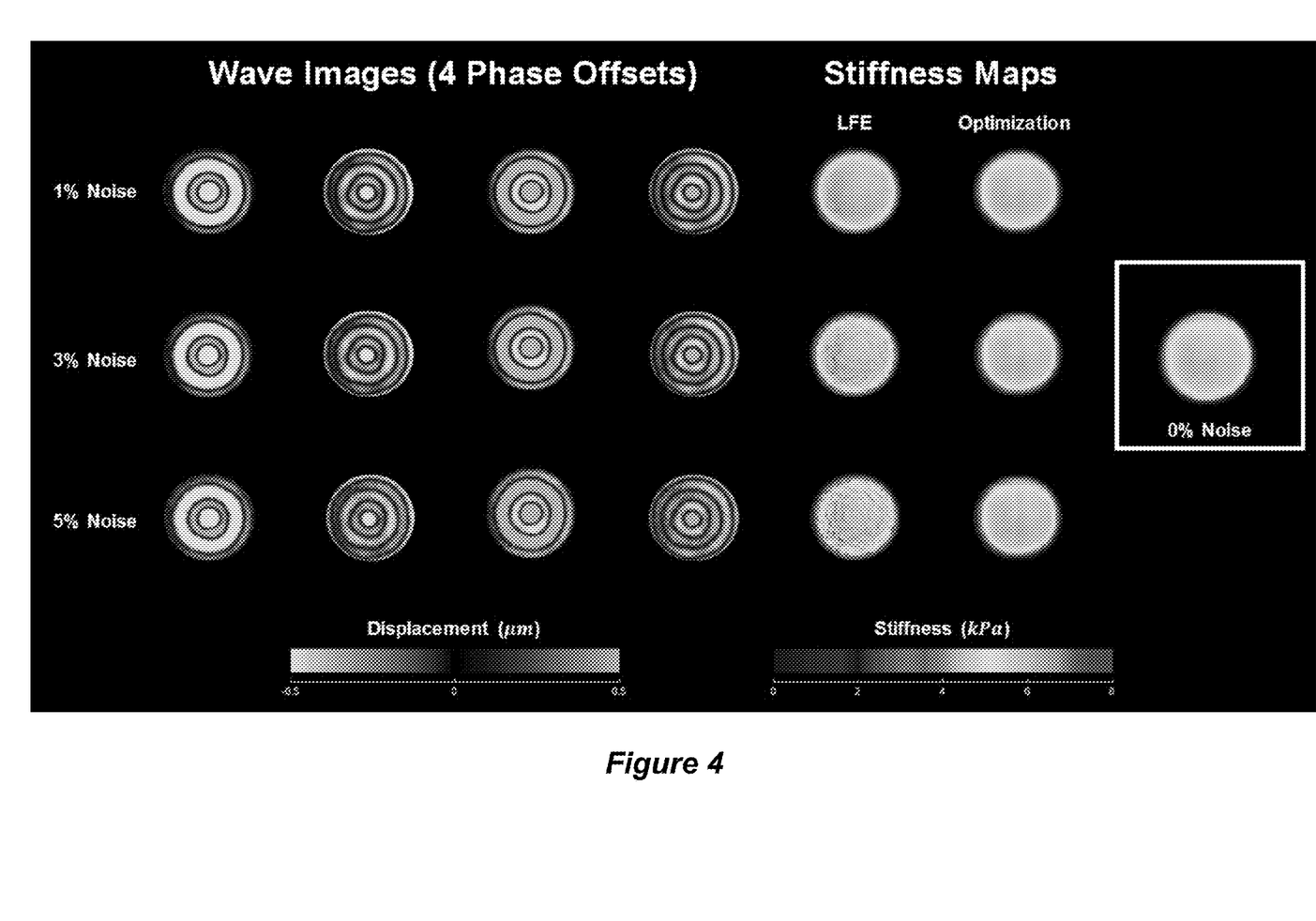
FIG. 4 demonstrates results of MRE measurements performed on a physical phantom, with wave images and the corresponding stiffness maps yielded by LFE and optimization methods according to embodiments of the present disclosure.

The optimization method according to embodiments of the present disclosure was less affected by the presence of noise in physical phantom data when compared to LFE. FIG. 4 demonstrates the noisy wave images, and stiffness maps obtained using both methods. More consistent and less noisy stiffness estimation was observed in optimization-derived results when compared to LFE-derived stiffness maps.

Figure 5:
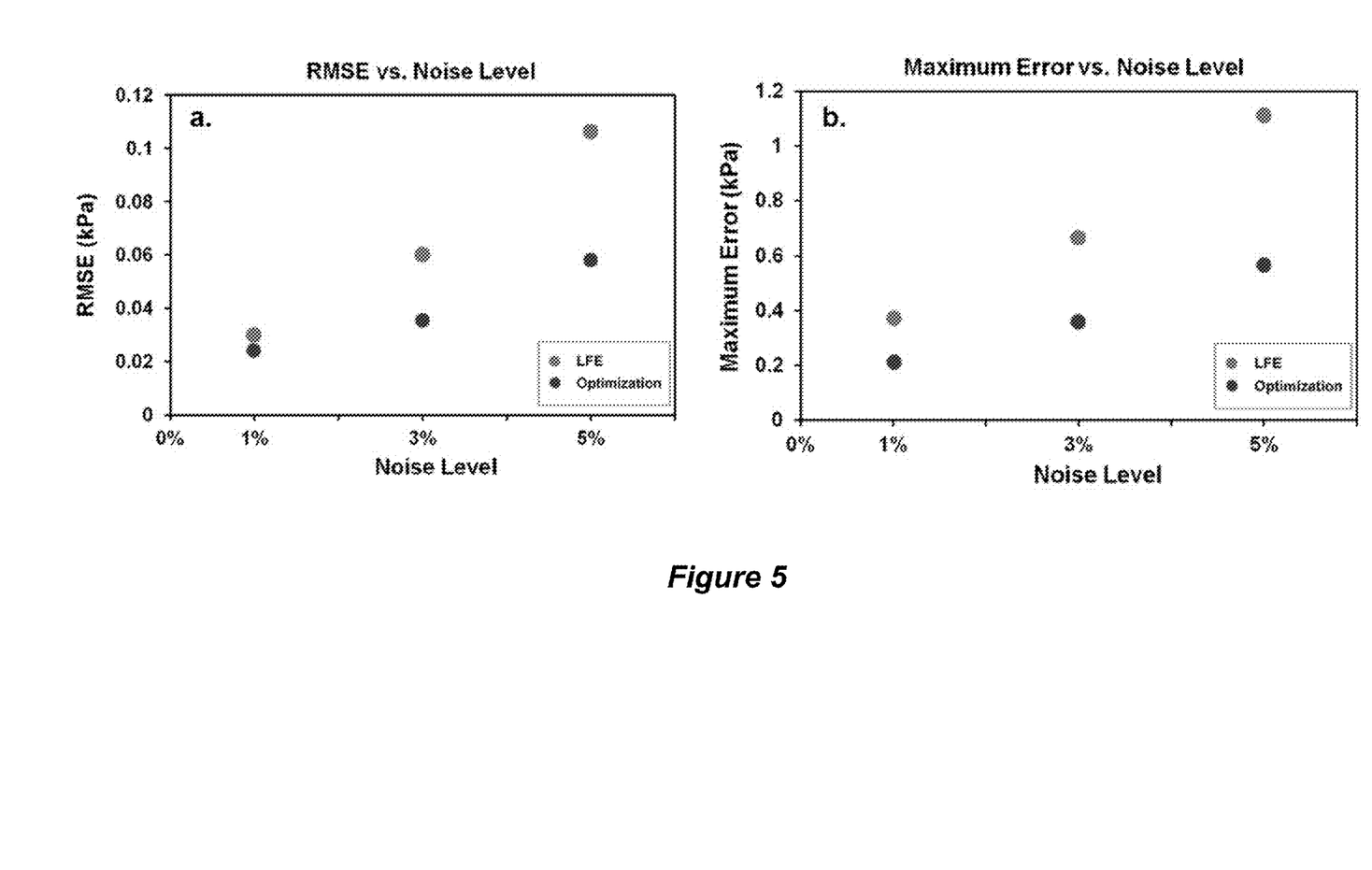
FIG. 5 illustrates a quantitative comparison of RMSE (see "a.") and maximum error (see "b.") of the optimization technique according to embodiments of the present disclosure compared to the LFE technique in the physical phantom data.

The optimization method according to this example implementation the present disclosure yielded lower RMSE and lower maximum error when compared to LFE technique in the physical phantom data. FIG. 5 displays the quantitative comparison of both methods.

According to the above-described example implementation corresponding results (EXAMPLE 1), an optimization technique in accordance with embodiments of the present disclosure yielded stiffness estimation with lower RMSE and lower maximum error when compared to LFE, demonstrating that the optimization technique disclosed is able to outperform LFE in the presence of noise.

Example 2

Performance on In Vivo Liver MRE

In this example implementation, two healthy volunteers were recruited for in vivo liver MRE. All MR imaging was performed on a 3T MR scanner (MAGNETOM Prisma, Siemens Healthcare, Erlangen, Germany) using standard clinical protocol of liver MRE. To test the performance of an unconstrained optimization inversion method according to embodiments of the present disclosure, under a noisy situation where the wave penetration is insufficient in the liver and the Octahedral Shear Strain-Based Signal-to-Noise Ratio (OSS SNR) is low, only 5% of the maximum power of the active driver (Resoundant driver, Resoundant Inc., Rochester, Minn.) (i.e., the wave generator) was used. The low wave penetration issue is commonly observed in clinical practice when the subject has a high body mass index (BMI) and the driver power is inadequate. Therefore, this situation was simulated using low driver power. The experiment was repeated 5 times for each volunteer. Subsequently, liver stiffness maps were calculated using an unconstrained optimization inversion method according to embodiments of the present disclosure and multi-model direct inversion (MMDI) method which is the current clinical gold standard.

Coefficient of variation (COV) was calculated from 5 repeated scans for both volunteers. COV is a measure of consistency of the stiffness calculation and a robust inversion method should yield low COV because the liver stiffness will not change in 5 repeat scans for each volunteer despite the presence of noise in the measured data.

Figure 6:
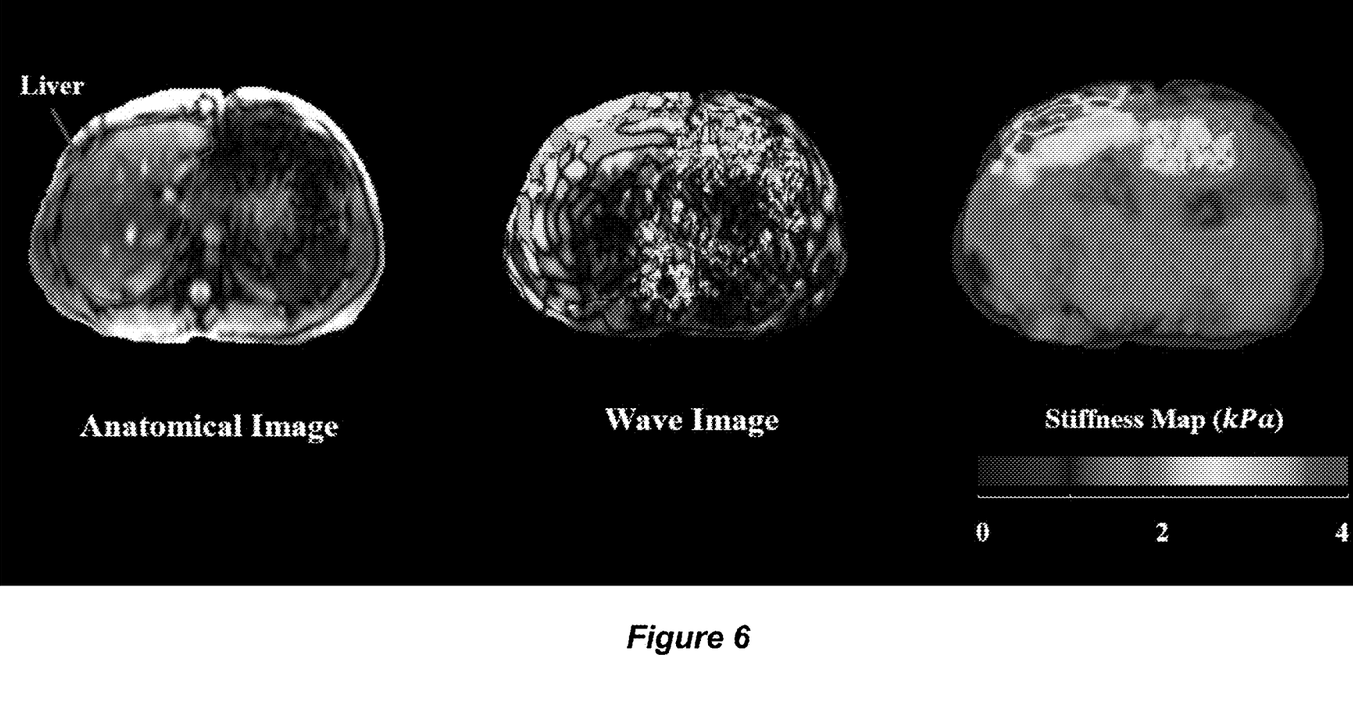
FIG. 6 illustrates aspects of an example implementation of in vivo liver MRE according to embodiments of the present disclosure, showing an anatomical image (left), wave image (center) and stiffness map (right).

FIG. 6 shows an anatomical image (left), wave image (center) and stiffness map (right) illustrating aspects of this example implementation (EXAMPLE 2). Table 2 below demonstrates the liver stiffness measurement when the measured data is noisy. The implemented unconstrained optimization inversion method according to embodiments of the present disclosure yields lower COV than MMDI, suggesting that methods according to the present disclosure is more robust to noise than MMDI when the MRE data does not have sufficient wave penetration.

TABLE 2

Liver Stiffness Measurement on 2 Volunteers

|  | Volunteer 1 Liver Stiffness (kPa) | | Volunteer 2 Liver Stiffness (kPa) | |
| --- | --- | --- | --- | --- |
|  | Example 2 Method | MMDI | Example 2 Method | MMDI |
| Repeat 1 | 2.15 | 2.14 | 1.83 | 1.85 |
| Repeat 2 | 2.29 | 2.20 | 1.81 | 1.80 |
| Repeat 3 | 2.17 | 1.99 | 1.83 | 1.87 |
| Repeat 4 | 2.14 | 2.05 | 1.82 | 1.90 |
| Repeat 5 | 2.21 | 2.21 | 1.80 | 1.85 |
| Coefficient of Variation | 2.89 | 4.50 | 0.86 | 2.00 |

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The patentable scope of certain embodiments of the present disclosure is indicated by the appended claims, rather than the foregoing description, and all changes that come within the meaning and range of equivalents thereof are intended to be embraced therein.

LIST OF REFERENCES

[1] Muthupillai R, Lomas D, Rossman P, Greenleaf J F. Magnetic resonance elastography by direct visualization of propagating acoustic strain waves. Science 1995; 269 (5232):1854-1856.
[2] Manduca A, Oliphant T E, Dresner M, Mahowald J, Kruse S A, Amromin E, Felmlee J P, Greenleaf J F, Ehman R L. Magnetic resonance elastography: Non-invasive mapping of tissue elasticity. Med Image Anal 2001; 5(4):237-254.
[3] Kruse S A, Smith J A, Lawrence A J, Dresner M A, Manduca A, Greenleaf, J F and Ehman R L. Tissue characterization using magnetic resonance elastography: preliminary results. Physics in medicine and biology 2000; 45(6):1579-1590.
[4] Papazoglou S, Hamhaber U, Braun J, and Sack I. Algebraic Helmholtz inversion in planar magnetic resonance elastography. Physics in medicine and biology 2008; 53(12):3147-3158.
[5] Oliphant T E, Manduca A, Ehman R L, and Greenleaf J F. Complex-valued stiffness reconstruction for magnetic resonance elastography by algebraic inversion of the differential equation. Magnetic resonance in Medicine 2001; 45(2): 299-310.
[6] Ting S T, Ahmad R, Jin N, Craft J, Serafim da Silveira J, Xue H, Simonetti O P. Fast implementation for compressive recovery of highly accelerated cardiac cine MII using the balanced sparse model. Magnetic Resonance in Medicine 2017; 77(4):1505-1515.
[7] Paige C C and Saunders M A, LSQR: An Algorithm for Sparse Linear Equations And Sparse Least Squares, ACM Trans. Math. Soft. 1982; 8:43-71.

What is claimed is:

1. A method, comprising:
acquiring magnetic resonance elastography (MRE) data corresponding to mechanical waves in tissue of interest of a subject, wherein the MRE data is associated with stiffness of the tissue of interest; and
generating, based on the MRE data, a stiffness map representing stiffness of the tissue, wherein generating the stiffness map comprises performing an unconstrained optimization cost function that is configured to reduce noise in the acquired MRE data and achieve inversion of the reduced-noise MRE data,
wherein the unconstrained optimization cost function comprises:

$$J(u, \mu) = \underset{u,\mu}{\mathrm{argmin}} \left\| \frac{1}{c} \mathrm{LoG}(u) * \mu - u \right\|_2^2 + \lambda_1 \|u - u0\|_2^2 + \lambda_2 \|\psi(\mu)\|_1$$

wherein LoG is the Laplacian of Gaussian operator, $c = -\rho\omega^2$, $\rho$ is density of the tissue of interest, $\omega$ is angular mechanical frequency associated with vibration of the tissue of interest, $\mu$ is the stiffness map of interest, u is pursued tissue displacement, u0 is measured tissue displacement from acquired MRE data, $\psi$ is a linear sparsifying transform, and $\lambda_1, \lambda_2$ are regularization coefficients.

2. The method of claim 1, wherein, in the unconstrained optimization cost function, reducing noise of the MRE data and achieving inversion of the reduced-noise MRE data comprises reducing noise from the MRE data while ensuring sparsity of the stiffness map in a sparsifying transform domain.

3. The method of claim 2, wherein the linear sparsifying transform is configured to ensure sparsity of the stiffness map in the sparsifying transform domain.

4. The method of claim 3, wherein the linear sparsifying transform is a wavelet transform, total variation transform, or Fourier transform.

5. The method of claim 4, wherein the linear sparsifying transform is one of:
a wavelet transform configured to ensure sparsity of the stiffness map in a wavelet domain;
a total variation transform configured to ensure sparsity of the stiffness map in a total variation domain; or
a Fourier transform configured to ensure sparsity of the stiffness map in a Fourier transform domain.

6. The method of claim 1, wherein the unconstrained optimization cost function comprises a regularization term configured to allow pursued tissue displacement to deviate from noisy displacement measured from MRE phase images reconstructed from the acquired MRE data.

7. The method of claim 1, wherein the method further comprises identifying, based on the stiffness map, a physiological condition of the subject.

8. The method of claim 7, wherein identifying the physiological condition of the subject based on the stiffness map comprises identifying a mechanical property change in the tissue.

9. The method of claim 8, wherein the mechanical property change comprises a stiffness change.

10. The method of claim 7, wherein the physiological condition comprises an abnormal condition of the tissue that is associated with disease.

11. The method of claim 1, wherein the method further comprises generating the mechanical waves in the tissue.

12. The method of claim 11, wherein generating the mechanical waves in the tissue comprises generating external periodic mechanical waves in the tissue.

13. A method, comprising:
acquiring, by magnetic resonance scanning using scanning device, magnetic elastography (MRE) data corresponding to mechanical waves in tissue of interest of a subject, wherein the MRE data is associated with stiffness of the tissue of interest;
generating, based on the MRE data, a stiffness map representing stiffness of the tissue of interest, wherein generating the stiffness map comprises performing an unconstrained optimization cost function that is configured to reduce noise in the acquired MRE data and achieve inversion of the reduced-noise MRE data;
identifying, based on the stiffness map, a mechanical property change in the tissue of interest; and
identifying, based on the mechanical property change, an abnormal condition of the tissue of interest,
wherein the unconstrained optimization cost function comprises:

$$J(u, \mu) = \operatorname*{argmin}_{\mu,u} \left\| \frac{1}{c} \nabla^2 u * \mu - u \right\|_2^2 + \lambda_1 \|u - u0\|_2^2 + \lambda_2 \|\psi(\mu)\|_1$$

wherein LoG is the Laplacian of Gaussian operator, $c=-\rho\omega^2$, $\rho$ is density of the tissue of interest, $\omega$ is angular mechanical frequency associated with vibration of the tissue of interest, $\mu$ is the stiffness map of interest, u is pursued tissue displacement, u0 is measured tissue displacement from acquired MRE data, $\psi$ is a linear sparsifying transform, and $\lambda_1$, $\lambda_2$ are regularization coefficients.

14. The method of claim 13, wherein, in the unconstrained optimization cost function, reducing noise of the MRE data and achieving inversion of the reduced-noise MRE data comprises reducing noise from the MRE data while ensuring sparsity of the stiffness map in a sparsifying transform domain.

15. The method of claim 14, wherein the unconstrained optimization cost function comprises a regularization term configured to allow pursued tissue displacement to deviate from noisy displacement measured from MRE phase images reconstructed from the acquired MRE data.

16. The method of claim 14, wherein the linear sparsifying transform is configured to ensure sparsity of the stiffness map in the sparsifying transform domain.

17. The method of claim 16, wherein the linear sparsifying transform is a wavelet transform, total variation transform, or Fourier transform.

18. A system, comprising:
a magnetic resonance device configured to acquire magnetic resonance elastography (MRE) data corresponding to mechanical waves in tissue of interest of a subject, wherein the MRE data is associated with stiffness of the tissue of interest; and
at least one processor coupled to the magnetic resonance device and configured to execute computer-readable instructions which cause the system to generate, based on the MRE data, a stiffness map representing stiffness of the tissue of interest,
wherein generating the stiffness map comprises performing an unconstrained optimization cost function that is configured to reduce noise in the acquired MRE data and achieve inversion of the reduced-noise MRE data,
wherein the unconstrained optimization cost function comprises:

$$J(u, \mu) = \operatorname*{argmin}_{\mu,u} \left\| \frac{1}{c} LoG(u) * \mu - u \right\|_2^2 + \lambda_1 \|u - u0\|_2^2 + \lambda_2 \|\psi(\mu)\|_1$$

wherein LoG is the Laplacian of Gaussian operator, $c=-\rho\omega^2$, $\rho$ is density of the tissue of interest, $\omega$ is angular mechanical frequency associated with vibration of the tissue of interest, $\mu$ is the stiffness map of interest, u is pursued tissue displacement, u0 is measured tissue displacement from acquired MRE data, $\psi$ is a linear sparsifying transform, and $\lambda_1$, $\lambda_2$ are regularization coefficients.

19. The system of claim 18, further comprising a wave generator configured to generate the mechanical waves in the tissue of interest of the subject.

20. The system of claim 18, wherein:
in the unconstrained optimization cost function, reducing noise of the MRE data and achieving inversion of the reduced-noise MRE data comprises reducing noise from the MRE data while ensuring sparsity of the stiffness map in a sparsifying transform domain;
the unconstrained optimization cost function comprises a regularization term configured to allow pursued tissue displacement to deviate from noisy displacement measured from MRE phase images reconstructed from the acquired MRE data; and
the linear sparsifying transform is configured to ensure sparsity of the stiffness map in a sparsifying transform domain.

21. The system of claim 18, wherein the at least one processor is configured to execute computer-readable instructions to identify, based on the stiffness map, a physiological condition of the subject.

* * * * *